(12) United States Patent　　(10) Patent No.: US 7,731,685 B2
Ragheb et al.　　(45) Date of Patent: Jun. 8, 2010

(54) COATED MEDICAL DEVICE

(75) Inventors: Anthony O. Ragheb, West Lafayette, IN (US); Brian L. Bates, Bloomington, IN (US); Scott E. Boatman, Bloomington, IN (US); David G. Burton, Bloomington, IN (US); Michael C. Hoffa, Ellettsville, IN (US); Darin G. Schaeffer, Bloomington, IN (US); Jason S. Sturgeon, Solsberry, IN (US)

(73) Assignees: Cook Incorporated, Bloomington, IN (US); MED Institute, Inc., West Lafayette, IN (US)

( * ) Notice: Subject to any disclaimer, the term of this patent is extended or adjusted under 35 U.S.C. 154(b) by 139 days.

(21) Appl. No.: 11/234,702

(22) Filed: Sep. 23, 2005

(65) Prior Publication Data

US 2006/0020331 A1　　Jan. 26, 2006

Related U.S. Application Data

(63) Continuation of application No. 10/618,977, filed on Jul. 14, 2003.

(60) Provisional application No. 60/395,434, filed on Jul. 12, 2002.

(51) Int. Cl.
*A61M 31/00* (2006.01)
(52) U.S. Cl. .............. 604/103.02; 604/103.06; 604/265; 604/509
(58) Field of Classification Search ........ 604/96.01, 604/103.02, 103.06, 103.11, 264, 265, 266, 604/500, 506–509
See application file for complete search history.

(56) References Cited

U.S. PATENT DOCUMENTS

| 3,699,956 | A | 10/1972 | Kitrilakis et al. |
|---|---|---|---|
| 4,101,984 | A | 7/1978 | MacGregor |
| 4,305,926 | A | 12/1981 | Everse et al. |
| 4,343,788 | A | 8/1982 | Mustacich et al. |
| 4,476,590 | A | 10/1984 | Scales et al. |
| 4,479,795 | A | 10/1984 | Mustacich et al. |

(Continued)

OTHER PUBLICATIONS

Dorothea I. Axel, PHD; Wolfgang Kunert, MD; Christoph Göggelmann; Martin Oberhoff, MD Christian Herdeg, MD Axel Küttner; Doris H. Wild; Bernhard R. Brehm, MD; Reimer Riessen, MD; Gerhard Köveker, MD; Karl R. Karsch, MD; Paclitaxel Inhibits Arterial Smooth Muscle Cell Proliferation and Migration In Vitro and in Vivo Using Local Drug Delivery; *Circulation*; 1997; 96:636-645.
Eric K. Rowinsky, MD, Ross C. Donehower, MD; Drug Therapy; *The New England Journal of Medicine*; Apr. 13, 1995; vol. 332 No. 15;1004-1014.
Charles, Roger et al., "Ceramide-Coated Balloon Catheters Limit Neointimal Hyperplasia After Stretch Injury in Carotid Arteries", Circ. Res. 2000; 87; 282-288, American Heart Association, Dallas, TX.

(Continued)

*Primary Examiner*—Kevin C Sirmons
*Assistant Examiner*—Bhisma Mehta
(74) *Attorney, Agent, or Firm*—Brinks Hofer Gilson & Lione

(57) ABSTRACT

A coated medical device adapted for introduction into a passage or vessel of a patient is provided. The medical device is preferably an implantable balloon with a bioactive deposited or within the balloon. The balloon can further include a hydrophilic material positioned between the balloon and a bioactive material posited on the balloon.

15 Claims, 11 Drawing Sheets

U.S. PATENT DOCUMENTS

| | | | |
|---|---|---|---|
| 4,502,159 A | 3/1985 | Woodroof et al. |
| 4,677,143 A | 6/1987 | Laurin et al. |
| 4,769,013 A | 9/1988 | Lorenz et al. |
| 4,793,825 A | 12/1988 | Benjamin et al. |
| 4,872,867 A | 10/1989 | Joh |
| 4,879,135 A | 11/1989 | Greco et al. |
| 4,886,062 A | 12/1989 | Wiktor |
| 4,909,799 A | 3/1990 | Thulesius et al. |
| 4,917,686 A | 4/1990 | Bayston et al. |
| 4,925,668 A | 5/1990 | Khan et al. |
| 4,950,256 A | 8/1990 | Luther et al. |
| 4,994,047 A | 2/1991 | Walker et al. |
| 5,004,461 A | 4/1991 | Wilson |
| 5,019,096 A | 5/1991 | Fox, Jr. et al. |
| 5,019,393 A | 5/1991 | Ito et al. |
| 5,019,601 A | 5/1991 | Allen |
| 5,053,048 A | 10/1991 | Pinchuk |
| 5,059,166 A | 10/1991 | Fischell et al. |
| 5,067,491 A | 11/1991 | Taylor, II et al. |
| 5,091,205 A | 2/1992 | Fan |
| 5,098,977 A | 3/1992 | Frautschi et al. |
| 5,102,402 A | 4/1992 | Dror et al. |
| 5,108,424 A | 4/1992 | Hoffman, Jr. et al. |
| 5,112,457 A | 5/1992 | Marchant |
| 5,135,516 A | 8/1992 | Sahatjian et al. |
| 5,163,952 A | 11/1992 | Froix |
| 5,165,952 A | 11/1992 | Solomon et al. |
| 5,171,217 A | 12/1992 | March et al. |
| 5,182,317 A | 1/1993 | Winters et al. |
| 5,197,977 A | 3/1993 | Hoffman, Jr. et al. |
| 5,217,493 A | 6/1993 | Raad et al. |
| 5,222,971 A | 6/1993 | Willard et al. |
| 5,229,172 A | 7/1993 | Cahalan et al. |
| 5,244,654 A | 9/1993 | Narayanan |
| 5,282,823 A | 2/1994 | Schwartz et al. |
| 5,298,255 A | 3/1994 | Sawamoto et al. |
| 5,304,121 A | 4/1994 | Sahatjian |
| 5,314,688 A | 5/1994 | Kauffman et al. |
| 5,324,261 A | 6/1994 | Amundson et al. |
| 5,342,348 A | 8/1994 | Kaplan |
| 5,344,411 A | 9/1994 | Domb et al. |
| 5,344,444 A | 9/1994 | Glastra |
| 5,345,933 A | 9/1994 | Peterson et al. |
| 5,348,873 A | 9/1994 | Matsuda et al. |
| 5,356,433 A | 10/1994 | Rowland et al. |
| 5,364,356 A | 11/1994 | Höfling |
| 5,380,299 A | 1/1995 | Fearnot et al. |
| 5,383,927 A | 1/1995 | De Goicoechea et al. |
| 5,383,928 A | 1/1995 | Scott et al. |
| 5,419,760 A | 5/1995 | Narciso, Jr. |
| 5,443,458 A | 8/1995 | Eury |
| 5,447,724 A | 9/1995 | Helmus et al. |
| 5,449,382 A | 9/1995 | Dayton |
| 5,454,886 A | 10/1995 | Burrell et al. |
| 5,455,040 A | 10/1995 | Marchant |
| 5,456,663 A | 10/1995 | Lemelson |
| 5,457,113 A | 10/1995 | Cullinan et al. |
| 5,464,450 A | 11/1995 | Buscemi et al. |
| 5,464,650 A | 11/1995 | Berg et al. |
| 5,498,238 A | 3/1996 | Shapland et al. |
| 5,500,013 A | 3/1996 | Buscemi et al. |
| 5,510,330 A | 4/1996 | Martin et al. |
| 5,531,716 A | 7/1996 | Luzio et al. |
| 5,534,288 A | 7/1996 | Gruskin et al. |
| 5,545,208 A | 8/1996 | Wolff et al. |
| 5,554,181 A | 9/1996 | Das |
| 5,562,922 A | 10/1996 | Lambert |
| 5,567,495 A | 10/1996 | Modak et al. |
| 5,569,463 A | 10/1996 | Helmus et al. |
| 5,578,075 A | 11/1996 | Dayton |
| 5,605,696 A | 2/1997 | Eury et al. |
| 5,607,463 A | 3/1997 | Schwartz et al. |
| 5,607,475 A | 3/1997 | Cahalan et al. |
| 5,609,629 A | 3/1997 | Fearnot et al. |
| 5,624,411 A | 4/1997 | Tuch |
| 5,628,730 A | 5/1997 | Shapland et al. |
| 5,629,008 A | 5/1997 | Lee |
| 5,634,901 A | 6/1997 | Alba et al. |
| 5,649,977 A | 7/1997 | Campbell |
| 5,674,192 A | 10/1997 | Sahatjian et al. |
| 5,679,400 A | 10/1997 | Tuch |
| 5,681,846 A | 10/1997 | Trissel |
| 5,697,967 A | 12/1997 | Dinh et al. |
| 5,707,385 A | 1/1998 | Williams |
| 5,709,874 A | 1/1998 | Hanson et al. |
| 5,716,981 A | 2/1998 | Hunter et al. |
| 5,733,327 A | 3/1998 | Igaki et al. |
| 5,733,925 A | 3/1998 | Kunz et al. |
| 5,738,901 A | 4/1998 | Wang et al. |
| 5,749,915 A | 5/1998 | Slepian |
| 5,762,638 A | 6/1998 | Shikani et al. |
| 5,770,198 A | 6/1998 | Coller et al. |
| 5,772,640 A | 6/1998 | Modak et al. |
| 5,820,607 A | 10/1998 | Tcholakian et al. |
| 5,824,049 A | 10/1998 | Ragheb et al. |
| 5,837,008 A | 11/1998 | Berg et al. |
| 5,843,089 A | 12/1998 | Sahatjian et al. |
| 5,853,745 A | 12/1998 | Darouiche |
| 5,868,719 A | 2/1999 | Tsukernik |
| 5,873,904 A | 2/1999 | Ragheb et al. |
| 5,886,026 A | 3/1999 | Hunter et al. |
| 5,902,283 A | 5/1999 | Darouiche et al. |
| 5,941,871 A | 8/1999 | Adams et al. |
| 5,964,730 A | 10/1999 | Williams et al. |
| 6,048,620 A | 4/2000 | Zhong ............... 428/424.4 |
| 6,096,070 A | 8/2000 | Ragheb et al. |
| 6,171,232 B1 | 1/2001 | Papadreou et al. |
| 6,240,616 B1 | 6/2001 | Yan |
| 6,273,908 B1 | 8/2001 | Ndondo-Lay |
| 6,273,913 B1 | 8/2001 | Wright et al. |
| 6,280,411 B1 | 8/2001 | Lennox |
| 6,287,285 B1 * | 9/2001 | Michal et al. ............. 604/264 |
| 6,299,604 B1 | 10/2001 | Ragheb et al. |
| 6,306,166 B1 | 10/2001 | Barry et al. |
| 6,335,029 B1 | 1/2002 | Kamath et al. |
| 6,369,039 B1 | 4/2002 | Palasis et al. ............... 514/44 |
| 6,419,692 B1 | 7/2002 | Yang et al. |
| 6,599,275 B1 | 7/2003 | Fischer, Jr. |
| 6,656,156 B2 | 12/2003 | Yang et al. |
| 6,730,064 B2 | 5/2004 | Ragheb et al. |
| 6,746,773 B2 * | 6/2004 | Llanos et al. ............... 428/421 |
| 6,774,278 B1 | 8/2004 | Ragheb et al. |
| 6,918,927 B2 * | 7/2005 | Bates et al. ............... 623/1.15 |
| 6,939,320 B2 | 9/2005 | Lennox |
| 2002/0032414 A1 | 3/2002 | Ragheb et al. |
| 2003/0028243 A1 | 2/2003 | Bates et al. |
| 2003/0028244 A1 | 2/2003 | Bates et al. |
| 2003/0036794 A1 | 2/2003 | Ragheb et al. |
| 2003/0059454 A1 * | 3/2003 | Barry et al. ............... 424/423 |
| 2003/0130716 A1 | 7/2003 | Weber et al. |
| 2004/0068241 A1 | 4/2004 | Fischer, Jr. |
| 2004/0073284 A1 | 4/2004 | Bates et al. |
| 2004/0243225 A1 | 12/2004 | Ragheb et al. |
| 2005/0042295 A1 | 2/2005 | Hunter et al. |
| 2005/0055078 A1 | 3/2005 | Campbell |
| 2005/0101522 A1 | 5/2005 | Speck et al. ............... 514/1 |
| 2005/0123605 A1 | 6/2005 | Hunter et al. |
| 2005/0222677 A1 | 10/2005 | Bates et al. |
| 2005/0278021 A1 | 12/2005 | Bates et al. ............... 623/1.44 |
| 2006/0020243 A1 | 1/2006 | Speck et al. ............ 604/103.02 |

* cited by examiner

COATED MEDICAL DEVICE

CROSS-REFERENCE TO RELATED APPLICATIONS

This application is a continuation of co-pending U.S. patent application Ser. No. 10/618,977, filed on Jul. 14, 2003, which claims priority to U.S. Provisional Application Ser. No. 60/395,434, filed Jul. 12, 2002; all of the above-referenced applications are incorporated by reference in their entirety.

TECHNICAL FIELD

This invention relates generally to human and veterinary medical devices and, more particularly, to coated medical devices incorporating drugs, bioactive agents, therapeutic agents or diagnostic agents.

BACKGROUND

It has become common to treat a variety of medical conditions by temporarily or permanently introducing a coated medical device, and, in particular, a coated medical implanted device partly or completely into the esophagus, trachea, colon, biliary tract, urinary tract, vascular system or other location within a human or veterinary patient. Many treatments of the vascular or other systems entail the introduction of a device such as a stent, a catheter, a balloon, a wire guide, a cannula or the like. For this purpose, a stent may most simply be considered as a cylinder of relatively short length which opens a body passage or lumen or which maintains a body passage or lumen in an open condition. In addition, balloons such as angioplasty or dilation balloons are expanded to open a body passage or vessel lumen, thereby causing potential trauma or injury to the expanded passage or vessel.

Such medical devices are generally capable of serving their intended purposes quite well. Some drawbacks can be encountered during their use, however. For example, when a device is introduced into and manipulated through the vascular system of a patient, the blood vessel walls can be disturbed or injured. Clot formation or thrombosis often results at the injured site, causing stenosis (closure) of the blood vessel. Moreover, if the medical device is left within the patient for an extended period of time, thrombus often forms on the device itself, again causing stenosis. As a result, the patient is placed at risk of a variety of complications, including heart attack, pulmonary embolism, and stroke. Thus, the use of such a medical device can entail the risk of precisely the problems that its use was intended to ameliorate.

When medical devices such as stents and, in particular, coated stents are implanted in a vessel lumen, edge effect trauma occurs to the tissue at and beyond the ends of the implanted stent. This trauma or injury can be the result of the implanted stent causing injury to the vessel wall. However, delivery of such an implanted stent normally includes the use of an inflatable balloon of which the stent is mounted thereon with the ends of the balloon extending axially beyond the ends of the stent. When the balloon is inflated to deliver the stent, the ends of the balloon extending beyond that of the stent inflate so as to dilate and injure the tissue extending beyond the ends of the stent. Should the stent be coated or include a therapeutic agent, the therapeutic or treatment agent can possibly cause injury to the tissue extending beyond the ends of the stent. This treatment could include a chemical, radiation, or biochemical agent or treatment. Furthermore, delivery agents such as polymers and the like used to deliver the treatment agent can also cause this edge effect reaction to the tissue extending beyond the ends of the implanted stent. However, it is to be understood that regardless of the cause of the trauma or injury to the vessel wall, the tissue will react such as with smooth muscle cell proliferation and the like thereby creating an adverse reaction and subsequent closure or stenosis of the vessel.

Another way in which blood vessels undergo stenosis is through disease. Probably the most common disease causing stenosis of blood vessels is atherosclerosis. Many medical devices and therapeutic methods are known for the treatment of atherosclerotic disease. One particularly useful therapy for certain atherosclerotic lesions is percutaneous transluminal angioplasty (PTA). During PTA, a balloon-tipped catheter is inserted in a patient's artery, the balloon being deflated. The tip of the catheter is advanced to the site of the atherosclerotic plaque to be dilated. The balloon is placed within or across the stenotic segment of the artery, and then inflated. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which PTA is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombic) directly into the arterial wall at the time of angioplasty could reduce the incidence of thrombotic acute closure, but the results of attempts to do so have been mixed.

A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling." It has similarly been postulated that the delivery of appropriate agents directly into the arterial wall could interrupt the cellular and/or remodeling events leading to restenosis. However, like the attempts to prevent thrombotic acute closure, the results of attempts to prevent restenosis in this manner have been mixed.

Non-atherosclerotic vascular stenosis may also be treated by PTA. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapies to treat or obviate them have been similarly disappointing.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are treatable with stents, catheters, cannulae and other medical devices inserted into the esophagus, trachea, colon, biliary tract, urinary tract and other locations in the body. A wide variety of bioactive materials (drugs, therapeutic agents, diagnostic agents and other materials having biological or pharmacological activity within a patient) have been applied to such medical devices for the purpose of introducing such materials into the patient. Unfortunately, the durable application of bioactive materials to stents and the like, sufficient for such introduction to successfully occur, is often problematic. A range of containment or layering materials have been applied to such devices to permit the timed release of bioactive materials from such devices, or even to permit bioactive materials to be applied to such devices at all. Unfortunately, the use of such containment materials can significantly increase the time and cost of manufacturing suitable implantable devices. Moreover, some bioactive materials may not be able to withstand incorporation in known containment materials. Additionally, certain containment materials may not be biocompatible and may cause problems of the type desired to be reduced.

It would be desirable to develop devices and methods for reliably delivering suitable therapeutic and diagnostic agents, drugs and other bioactive materials directly into a body portion during or following a medical procedure, so as to treat or prevent the conditions and diseases mentioned above, for example, to prevent abrupt closure and/or restenosis of a body portion such as a passage, lumen or blood vessel. It would also be desirable to limit systemic exposure of the patient to such bioactive materials. This would be particularly advantageous in therapies involving the delivery of a chemotherapeutic agent to a particular organ or site through an intravenous catheter (which itself has the advantage of reducing the amount of agent needed for successful treatment), by preventing stenosis both along the catheter and at the catheter tip. It would be desirable to similarly improve other therapies. Of course, it would also be desirable to avoid degradation of the agent, drug or bioactive material during its incorporation on or into any such device. It would further be highly desirable to develop a method for coating an implantable medical device with a drug, therapeutic agent, diagnostic agent or other bioactive material which entailed a minimum number of steps, thereby reducing the ultimate cost of treating the patient. It would be desirable to deliver the bioactive material without causing additional problems with a poor biocompatible carrier or containment material. Finally, it would be highly desirable to develop a method for coating an implantable medical device with a drug, therapeutic agent, diagnostic agent or other bioactive material which could be carried out in such a way as to minimize any environmental or personal risks or inconveniences associated with the manufacture of the device.

In addition, it is desirable to develop devices and methods for delivering a suitable therapeutic and diagnostic agent, drugs and other bioactive materials to those areas of the passage or vessel just beyond, for example, the ends of an implanted coated stent to treat, minimize or preferably eliminate edge effects that ultimately cause trauma to the vessel wall and subsequent occlusion or stenosis of the vessel. Similarly, it would be desirable to provide such a medical device for treating passage or vessel tissue that has been affected by a previously implanted device.

SUMMARY

The foregoing problems are solved and a technical advance is achieved in an illustrative embodiment of a coated medical device of the present invention in which a drug, therapeutic agent, diagnostic agent or other bioactive or pharmacologically active material is delivered or applied directly to the surface of the passage or vessel wall. In one illustrative embodiment, the coated medical device comprises an expandable balloon on which a bioactive material is applied and coats the outer surface of the expandable balloon. In a preferred illustrative embodiment, the bioactive material is a lipophilic material such as paclitaxel or dexamethasone which is an anti-inflammatory steroid for attachment to the cell wall. This lipophilic bioactive material is attracted by the cell membrane of the endothelial cells of the inner wall and initially adheres to these cells when put in contact therewith. The lipophilic material is then drawn or transferred into the cell membrane. In addition, when the endothelial cells are injured or removed from the inner wall, smooth muscle cells are then exposed which also include lipids and attract the lipophilic bioactive material. The delivery and/or attachment of this lipophilic bioactive material is preferably accomplished by bringing the lipophilic bioactive material in physical or direct contact with the endothelial or smooth muscle cells. Thus, the medical device of the present invention not only includes preferably an expandable balloon but an expandable balloon with a coating of the preferred lipophilic bioactive material. When the balloon is expanded at the treatment site, the coating material and, in particular, the lipophilic bioactive material is brought into direct or physical contact with the inner wall cells of the vessel and thus transferred from the balloon to the desired passage or vessel wall cells. When transferring the preferred lipophilic bioactive material to the vessel wall, preferred inflation times of up to and about one minute are used in delivering the lipophilic bioactive material. To further improve the treatment of the vessel wall and transfer the bioactive material thereto, a hydrophilic material is applied to the base material of the device of which the preferred lipophilic bioactive material is applied or coated thereon. This hydrophilic material, also known as a slip coating lessens the adhesion of the base material to the lipophilic bioactive material and helps facilitate a delivery of the lipophilic material to the vessel cells at the delivery site. In addition, blood for example, helps wet the slip coating and further enhance the delivery of the lipophilic bioactive material to the vessel wall. Thus, by selecting the ratio of lipophilic to hydrophilic coating materials, the delivery of the lipophilic material to the vessel walls can be better controlled. This ratio can be altered depending on the particular type of base material of the delivery device and the particular bioactive material being delivered to the vessel wall.

The medical device of the present invention such as a balloon is coated with the preferred lipophilic bioactive material with the balloon in an expanded or inflated condition. Thus, a larger and more complete dose of the lipophilic material can be applied to the outer surface of the balloon. The balloon is then deflated or evacuated so that the balloon wall material can be folded and assume its smallest outer diameter for insertion into the vessel or for placement of another device such as a coated stent over the folded outer surface of the balloon. The medical device such as the stent may also be coated with a bioactive substance for minimizing any undesirable response to the traumatized or stenotic vessel wall. In another preferred embodiment of the present invention, another layer of bioactive material such as a lipophilic bioactive material is applied and/or coated over the folded balloon and medical device such as a stent mounted on the balloon. Advantageously, this increases the amount of bioactive material that can be delivered to the vessel wall to treat and minimize adverse reactions due to treatment of the vessel tissue. When the balloon and stent are delivered to the treatment site, the balloon is inflated to expand and deliver the stent to the treatment site. Thus, the bioactive material is brought in direct contact with the vessel wall not only with the stent but with the balloon coming in contact with the vessel wall extending beyond the ends of the stent. Thus, the preferred lipophilic bioactive material is applied to the vessel wall extending beyond the ends of the implanted stent and thus minimizing, if not eliminating, the undesirable edge effect or restenosis that is often observed with the implantation of stents not utilizing material on the balloon for the delivery process. Advantageously, the application or coating of the balloon material in an inflated condition allows for a full application of the bioactive material between the folds of the balloon and thus full circumferential delivery of the lipophilic bioactive material to the inner surface of the vessel.

The foregoing problems are solved and a technical advance is achieved in an illustrative embodiment of a medical device of the present invention coated (at least in part) with a drug, therapeutic agent, diagnostic agent or other bioactive or pharmacologically active material. (Hereinafter, any or all of these will be collectively referred to as "a bioactive material" or "bioactive materials.") The specific improvement of the present invention entails attaining a desired surface roughness, or texturing, on the surface of the device by whatever treatment of the surface and applying the bioactive material directly to that roughened or textured surface without the need of any further overlying or containment layer or coating. Unexpectedly, this straight-forward expedient yields a coated implantable medical device which is sufficiently durable to withstand the desired implantation without suffering an unacceptable amount of loss (if any) of bioactive material from the device. In one aspect of the invention, at least a part of the surface of the device, for example the outer surface of a stent, is treated to produce a roughened, uneven, or unsmooth surface, and the bioactive material is formed or posited on at least the part of the surface. The degree of surface treatment is controlled to provide sufficient adhesion of the bioactive material to the device surface.

In the preferred embodiment of the medical device of the present invention, the device first comprises a structure adapted for temporary or permanent introduction into the esophagus, trachea, colon, biliary tract, urinary tract, vascular system or other location in a human or veterinary patient. The structure comprises a base material (preferably non-porous) having a roughened or textured surface. The surface of the base material can be roughened or textured by etching but is preferably roughened or textured by abrasion with an abrasive grit, most preferably sodium bicarbonate (USP).

The medical device of the present invention also comprises a layer of bioactive material posited directly upon the roughened or textured surface of the base material of the structure. Furthermore, the device advantageously does not require or is free of any additional coating or layer atop the layer of bioactive material.

As described in more detail below, the base material of the structure and the bioactive material posited on that base material can comprise any of a wide range of suitable materials. The selection of a specific combination of base material, bioactive material and surface roughness or texture depends upon the intended use of the medical device. Although texture may have a meaning of a repeatable pattern, this is clearly not the intent. The surface of the stent is that of any topography, whether repeatable or not, that helps improve adhesion of the bioactive material on the base material or modification thereof. Hereinafter, a textured surface will include a roughened, uneven, or unsmooth surface. The suitability of a chosen combination can readily be determined by an adhesion test which simulates the actual delivery of bioactive material during introduction and deployment of the device in a patient. Such a test is straightforward and is believed not to entail an undue amount of experimentation, particularly in comparison to the amount and technical level of testing required before a product of this type can be marketed in the United States.

The medical device of the present invention and its method of manufacture have several advantages over prior stents and other medical devices and methods for manufacturing them. The time and cost of manufacture of the medical device are minimized by the absence of any steps to incorporate the bioactive material in a containment layer, or to apply a containment or time-release layer over the bioactive material. The particularly preferred use of sodium bicarbonate as the abrasive to treat, roughen, or texture the surface of the base material of the structure enjoys several indirect cost savings resulting from the low toxicity of the sodium bicarbonate to production workers, the ease of product and waste cleanup, and the biocompatibility of any residual sodium bicarbonate. Worker safety and ease of product and waste cleanup are, of course, important advantages in their own right.

In a first aspect, then, the present invention is directed to a medical device comprising: a structure adapted for introduction into a patient, the structure comprising a base material (preferably non-porous) having a at least one of a roughened, uneven, unsmooth, or textured surface; and a layer of a bioactive material posited directly upon the surface of the base material of the structure. Furthermore, the medical device does not require or is free of any additional coating or layer atop the layer of bioactive material for delivering the bioactive material. The structure is preferably configured as a stent, such as a vascular or other stent. In another aspect of this invention, the medical device is a delivery device such as an expandable balloon of which a stent is mounted thereon. The balloon material is treated so as to be capable of delivering the bioactive material to the treatment site. The balloon material preferably includes a polyamide such as nylon or nylon 12 for applying the bioactive material directly thereto. As previously suggested, a hydrophilic slip coating can be applied to the surface of the medical delivery device to further facilitate the delivery and attachment of the lipophilic bioactive material to the vessel wall. Other balloon materials include PEBAX, polyethylene or irradiated polyethylene which has a smooth or slippery surface.

The base material of the structure preferably comprises at least one of: stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

The bioactive material of the layer on the roughened, uneven, unsmooth, or textured surface of the base material preferably comprises at least one of: paclitaxel; estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine or another antiplatelet agent; colchicine or another antimitotic, or another microtubule inhibitor; cytochalasin or another actin inhibitor; a remodeling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; $^{60}$Co (having a half life of 5.3 years), $^{192}$Ir (73.8 days), $^{32}$P (14.3 days), $^{111}$In (68 hours), $^{90}$Y (64 hours), $^{99}$mTc (6 hours) or another radio-therapeutic agent; iodine-containing compounds, barium-containing compounds, gold, tantalum, platinum, tungsten or another heavy metal functioning as a radiopaque agent; a peptide, a protein, an enzyme, an extra-cellular matrix component, a cellular component or another biologic agent; captopril, enalapril or another angiotensin converting enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a $^{14}$C-, $^{3}$H-, $^{131}$I-, $^{32}$P- or $^{36}$S-radio-labelled form or other radiolabelled form of any of the foregoing; or a mixture of any of these.

Preferably, the roughened, uneven, unsmooth, or textured surface of the base material of the structure has a mean surface roughness of about 10 μin. (about 250 nm) and a surface roughness range between about 1 μin. and about 100 μin. (about 25 nm and about 2.5 μm).

In a second aspect, the present invention is directed to a medical device comprising: a structure adapted for introduction into a patient, the structure comprising a base material having a roughened, uneven, unsmooth, or textured surface, the structure being configured as a vascular stent and the base material comprising at least one of stainless steel, nitinol, or an alloy of nickel and titanium; and a layer of a bioactive material posited directly upon the roughened or textured surface of the base material of the structure, the bioactive material comprising paclitaxel; wherein the medical device does not require or is free of any additional coating or layer atop the layer of bioactive material; and wherein the roughened or textured surface of the base material of the structure has a mean surface roughness of about 10 μin. (about 250 nm) and a surface roughness range between about 1 μin. and about 100 μin. (about 25 nm and about 2.5 μm).

In a third aspect, the present invention is directed to a method of manufacturing a medical device comprising the steps of: providing a structure adapted for introduction into a patient, the structure comprising a base material (preferably non-porous) having a surface; roughening or texturing the surface of the base material of the structure; and positing a layer of a bioactive material directly upon the roughened or textured surface of the base material of the structure; the method being characterized in that the resulting medical device does not require or is free of any additional coating or layer atop the layer of bioactive material.

Preferably, the method is carried out with a structure configured as a stent, such as a vascular stent. The method is preferably carried out with a base material and a bioactive material as described in the first aspect of the invention above.

The positing step of the method is preferably carried out by spraying a solution of the bioactive material on the roughened or textured surface of the base material of the structure. Dipping the base material in a solution of the bioactive material is also contemplated in the practice of the present invention.

The roughening or texturing step of the method is preferably carried out by abrading the surface of the base material of the structure. Etching of the surface is also contemplated in the practice of the present invention.

Abrading of the surface of the base material is preferably carried out with an abrasive grit comprising at least one of sodium bicarbonate (USP), calcium carbonate, aluminum oxide, colmanite (calcium borate), crushed glass or crushed walnut shells. More preferably, the abrading is carried out with an abrasive grit having a particle size of about 5 microns (5 μm) to about 500 microns (500 μm). Even more preferably, the abrading is carried out with sodium bicarbonate (USP) having a nominal particle size of about 50 microns (50 μm).

Abrading of the surface of the base material is preferably carried out with an abrasive grit delivered at a pressure under flow of about 5 to about 200 PSI (about 34 to about 1380 KPa) and at a grit feed rate of about 1 to about 1000 g/min. Abrading of the surface is preferably carried out so as to yield a textured surface on the base material having a mean surface roughness of about 10 μin. (about 250 nm) and a surface roughness range between about 1 μin. and about 100 μin. (about 25 nm and about 2.5 μm).

In another aspect, the present invention is directed to the product of the method described in the third aspect of the invention, above. In yet a further aspect, the present invention is directed to a method of medical treatment or diagnosis which comprises introducing the medical device of the present invention, or the product of the method of the present invention, into a human or veterinary patient.

Again, as indicated above, the medical device of the present invention and its method of manufacture have several advantages over prior stents and other medical devices and methods for manufacturing them. The time and cost of manufacture of the medical device of the present invention are minimized by the absence of any steps to incorporate the bioactive material in a containment layer, or to apply a containment or time-release layer over the bioactive material. The particularly preferred use of sodium bicarbonate as the abrasive to roughen or texture the surface of the base material of the structure enjoys cost savings resulting from the low toxicity of the sodium bicarbonate to production workers, the ease of product and waste cleanup, and the biocompatibility of any residual sodium bicarbonate. It should go without saying that the good worker safety and ease of product and waste cleanup enjoyed by the method of the present invention are highly desirable advantages, without regard to any costs saved.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

With reference now to the Figures, an implantable medical device 10 in accordance with the present invention is shown. The medical device 10 of the present invention first comprises a structure 12 adapted for temporary or permanent introduction into a human or veterinary patient. "Adapted" means that the structure 12 is particularly configured, shaped and sized for such introduction. By way of example, the structure 12 is most preferably configured as a vascular stent adapted for insertion into the vascular system of the patient.

The structure 12 can of course be particularly configured for use in other systems and sites such as the esophagus, trachea, colon, biliary ducts, urethra and ureters, among others. Indeed, the structure 12 can alternatively be configured as any conventional vascular or other comparable medical device, and can include any of a variety of conventional stent or other adjuncts, such as helically wound strands, perforated cylinders or the like. Moreover, because the problems addressed by the present invention arise primarily with respect to those portions of the device actually positioned within the patient, the inserted structure 12 need not be an entire device, but can merely be that portion of a vascular or other device which is intended to be introduced into the patient. Accordingly, the structure 12 can be configured as at least one of, or any portion of, a catheter, a wire guide, a cannula, a stent, a vascular or other graft, a cardiac pacemaker lead or lead tip, a cardiac defibrillator lead or lead tip, a heart valve, a suture, a needle, an angioplasty device or a pacemaker. The structure 12 can also be configured as a combination of portions of any of these.

Figure 1:
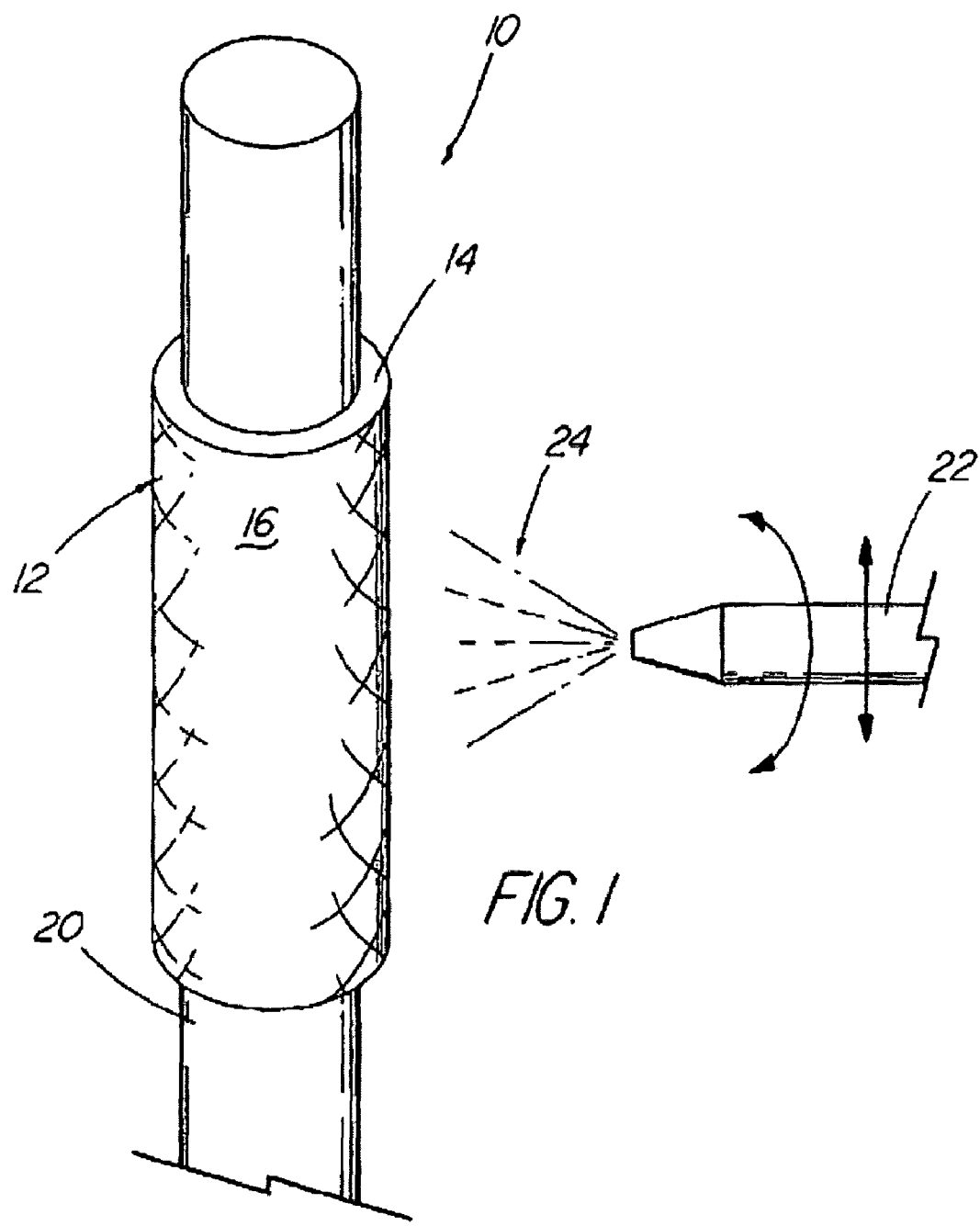
FIG. 1 is a side view showing one of the steps of the method of the preferred embodiment of the present invention.
Figure 2:
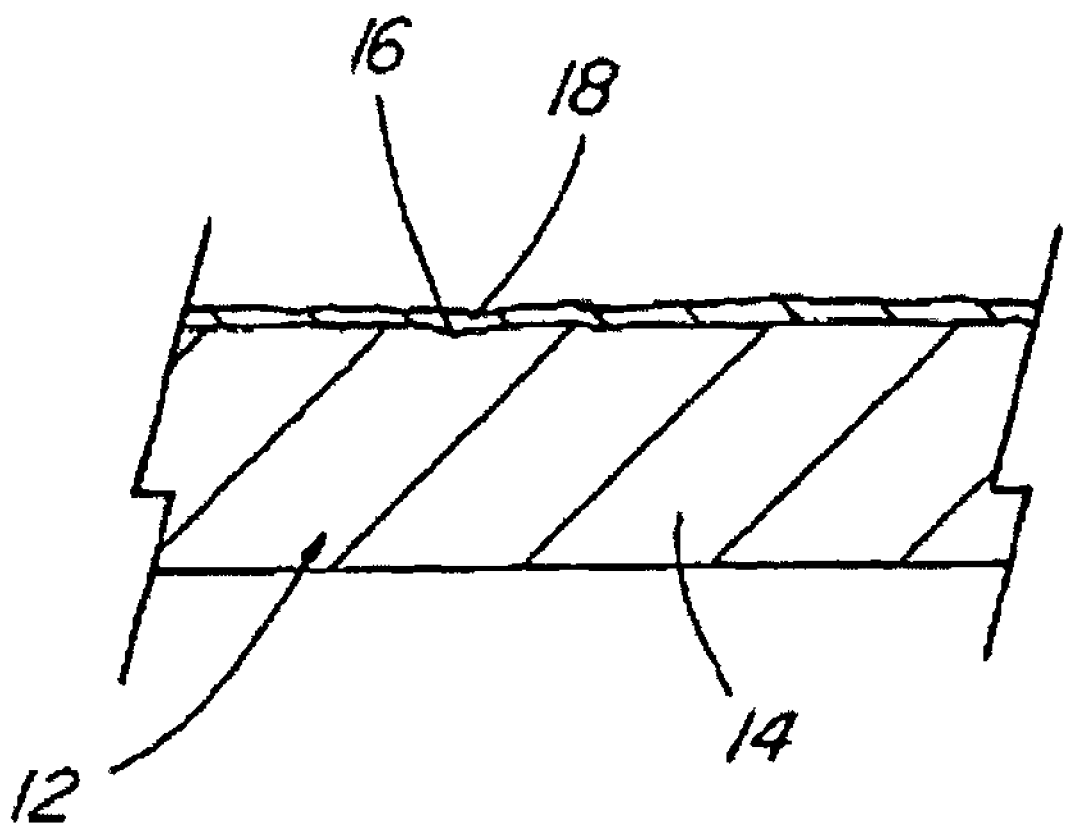
FIG. 2 is an enlarged cross-sectional view of a portion of the medical device and product of the preferred embodiment of the present invention.

For ease of understanding the present invention, FIGS. 1 and 2 show only a structure 12 configured as a stent, and more particularly, a vascular stent. More preferably, the structure 12 is configured as a vascular stent such as the LOGIC® stent, the V-FLEX PLUS® stent, or the ACHIEVE® stent, all commercially available from Cook Incorporated, Bloomington, Ind. Such stents are cut from a cannula of suitable material and possess a plurality of interconnected struts allowing the stents to expand upon inflation of a balloon on which they are carried. They possess a flat outer surface, which as a practical matter makes them easier to process via the present invention than stents made of a plurality of round wires; the latter are more difficult to abrade. These stents possess a smooth inside surface to reduce the possibility of thrombogenesis.

The particular shape and dimensions of the structure 12 should of course be selected as required for its specific purpose and for the particular site in the patient at which it will be employed, such as in the coronary arteries, aorta, esophagus, trachea, colon, biliary tract or urinary tract. A structure 12 intended for each location will have different dimensions particularly suited to such use. For example, aortic, esophageal, tracheal and colonic stents may have diameters up to about 25 mm and lengths about 100 mm or longer. Vascular stents are generally shorter, typically about 10 to 60 mm in length, and often preferably about 12 to 25 mm in length. Such vascular stents are typically designed to expand to a diameter of about 2 to 6 mm when inserted into the vascular system of a patient, often preferably about 2 to 4 mm.

The structure 12 is composed of a base material 14 suitable for the intended use of the structure 12. The base material 14 is preferably biocompatible. A variety of conventional materials can be employed as the base material 14. Some materials may be more useful for structures other than the coronary stent exemplifying the structure 12. The base material 14 may be either elastic or inelastic as required for its intended use in the patient. The base material may be either biodegradable or non-biodegradable, and a variety of biodegradable polymers are known. The base material 14 can also be porous or preferably non-porous, again based on its intended use or application.

Accordingly, the base material 14 can include at least one of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Stainless steel is particularly useful as the base material 14 when the structure 12 is configured as a vascular stent. In the practice of the present invention, however, particularly preferred base materials 14 include stainless steel, nitinol, tantalum, polylactic acid, polyglycolic acid and biodegradable materials. Molybdenum-rhenium alloy and magnesium may also possibly be useful base materials 14 as well.

Of course, when the structure 12 is composed of a radiolucent material such as polypropylene, polyethylene or others above, a conventional radiopaque marker or coating may and preferably should be applied to it at some limited location. The radiopaque marker or coating provides a means for identifying the location of the structure 12 by X-ray or fluoroscopy during or after its introduction into the patient's vascular system.

The base material 14 of the structure 12 of the medical device 10 of the present invention includes a roughened or textured surface 16 extending at least partly over the base material 14. The surface 16 is roughened or textured in a manner described in more detail below. While the surface 16 can be the entire surface of the base material 14, in the preferred embodiment of the present invention (where the structure 12 is configured as a vascular stent) the surface 16 is the outer surface of the base material 14.

The medical device 10 of the present invention further comprises at least one layer 18 of a bioactive material posited directly upon the roughened or textured surface 16 of the base material 14 of the structure 12. The medical device 10 of the present invention is characterized in that it does not require or is free of any additional coating or layer atop the layer 18 of bioactive material. Although, it is to be understood that for any reason an additional coating or layer atop or below the layer 18 of bioactive is desired, such coating or layer can be applied and still be within the contemplation of the present invention. The layer 18 may be smoother or rougher than the roughened or textured surface 16.

The base material 14 of the structure 12 is preferably non-porous, although the structure 12 itself can be perforate. The difference between a porous material and a non-porous but perforate material is a practical one; the relatively smaller open cells of a porous material are of a character and number sufficient to retain an appreciable amount of an applied bioactive material therein, while the relatively larger perforations of a non-porous material are of a character and number which are not sufficient to retain an appreciable amount of an applied bioactive material therein. Alternatively, the open cells of a porous material can be considered generally microscopic, while perforations through a non-porous material can be considered generally macroscopic.

A vast range of drugs, medicants and materials can be employed as the bioactive material in the layer 18. Particularly useful in the practice of the present invention are materials which prevent or ameliorate abrupt closure and restenosis of blood vessels previously opened by stenting surgery or other procedures. Thrombolytics (which dissolve, break up or disperse thrombi) and antithrombogenics (which interfere with or prevent the formation of thrombi) are especially useful bioactive materials when the structure 12 is a vascular stent. Particularly preferred thrombolytics are urokinase, streptokinase and the tissue plasminogen activators. Particularly preferred antithrombogenics are heparin, hirudin and the antiplatelets.

Urokinase is a plasminogen activating enzyme typically obtained from human kidney cell cultures. Urokinase catalyzes the conversion of plasminogen into the fibrinolytic plasmin, which breaks down fibrin thrombi.

Heparin is a mucopolysaccharide anticoagulant typically obtained from porcine intestinal mucosa or bovine lung. Heparin acts as a thrombin inhibitor by greatly enhancing the effects of the blood's endogenous antithrombin III. Thrombin, a potent enzyme in the coagulation cascade, is key in catalyzing the formation of fibrin. Therefore, by inhibiting thrombin, heparin inhibits the formation of fibrin thrombi.

Of course, bioactive materials having other functions can also be successfully delivered by the device 10 of the present invention. For example, an antiproliferative agent such as methotrexate will inhibit over-proliferation of smooth muscle cells and thus inhibit restenosis of the dilated segment of the blood vessel. Additionally, localized delivery of an antiproliferative agent is also useful for the treatment of a variety of malignant conditions characterized by highly vascular growth. In such cases, the device 10 of the present invention could be placed in the arterial supply of the tumor to provide a means of delivering a relatively high dose of the antiproliferative agent directly to the tumor.

A vasodilator such as a calcium channel blocker or a nitrate will suppress vasospasm, which is common following angioplasty procedures. Vasospasm occurs as a response to injury of a blood vessel, and the tendency toward vasospasm decreases as the vessel heals. Accordingly, the vasodilator is desirably supplied over a period of about two to three weeks. Of course, trauma from angioplasty is not the only vessel injury which can cause vasospasm, and the device 10 may be introduced into vessels other than the coronary arteries, such as the aorta, carotid arteries, renal arteries, iliac arteries or peripheral arteries for the prevention of vasospasm in them.

A variety of other bioactive materials are particularly suitable for use when the structure 12 is configured as something other than a coronary stent. For example, an anti-cancer chemotherapeutic agent can be delivered by the device 10 to a localized tumor. More particularly, the device 10 can be placed in an artery supplying blood to the tumor or elsewhere to deliver a relatively high and prolonged dose of the agent directly to the tumor, while limiting systemic exposure and toxicity. The agent may be a curative, a pre-operative debulker reducing the size of the tumor, or a palliative which eases the symptoms of the disease. It should be noted that the bioactive material in the present invention is delivered across the device 10, and not by passage from an outside source through any lumen defined in the device 10, such as through a catheter employed for conventional chemotherapy. The bioactive material of the present invention may, of course, be released from the device 10 into any lumen defined in it, and that lumen may carry some other agent to be delivered through it.

Paclitaxel is a particularly preferred anti-cancer agent and/or anti-angiogenic agent as the bioactive material of the layer 18. Paclitaxel is also a lipophilic bioactive material that is attracted by the lipids in the endothelial and smooth muscle wall cells of the vessel. When applied to the implantable medical device such as a stent of the present invention, the stent maintains the bioactive material layer 18 in direct contact with the vessel wall. In another aspect which will be hereinafter described, Paclitaxel is applied to a medical device such as a balloon which is used for delivering another medical device such as a stent to a treatment site. The Paclitaxel coating on the balloon material is then brought in direct contact of the vessel wall for only that period of the inflation of the balloon which is typically in the neighborhood of approximately one minute. The angiogenesis-dependent diseases are those diseases which require or induce vascular growth, for example, certain types of cancer. Estrogen and estrogen derivatives are also particularly preferred as the bioactive material of the layer 18.

Dopamine or a dopamine agonist such as bromocriptine mesylate or pergolide mesylate is useful for the treatment of neurological disorders such as Parkinson's disease. The device 10 could be placed in the vascular supply of the thalamic substantia nigra for this purpose, or elsewhere, localizing treatment in the thalamus.

The present invention also contemplates the use of bioactive materials which covalently bond to the roughened or textured surface 16 of the base material 14 of the structure 12.

It should be clear that a wide range of other bioactive materials can be delivered by the device 10. Accordingly, it is preferred that the bioactive material of the layer 18 comprises at least one of: paclitaxel; estrogen or estrogen derivatives; heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine or another antiplatelet agent; colchicine or another antimitotic, or another microtubule inhibitor; cytochalasin or another actin inhibitor; a remodeling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; an immunosuppressive agent (such as cyclosporine or rapamycin); an antibiotic (such as streptomycin, erythromycin or vancomycin); dopamine, bromocriptine mesylate, pergolide mesylate or another dopamine agonist; $^{60}$Co (having a half life of 5.3 years), $^{192}$Ir (73.8 days), $^{32}$P (14.3 days), $^{111}$In (68 hours), $^{90}$Y (64 hours), $^{99}$mTc (6 hours) or another radio-therapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a $^{14}$C-, $^{3}$H-, $^{131}$I-, $^{32}$P- or $^{36}$S-radiolabelled form or other radiolabelled form of any of the foregoing; or a mixture of any of these.

When the structure 12 is configured as a vascular stent, however, particularly preferred materials for the bioactive material of the layer 18 are heparin, anti-inflammatory steroids including but not limited to dexamethasone and its derivatives, and mixtures of heparin and such steroids.

Other materials may possibly be useful as the bioactive material in the practice of the present invention, including: smooth muscle cell inhibitors, collagen inhibitors, anti-coagulants and cholesterol reducing agents; forskolin, vapiprost, prostaglandin and analogues thereof, prostacyclin and prostacyclin analogues, dextran and dipyridamole; angiotensin converting enzyme inhibitors such as Captopril® (available from Squibb), Cilazapril® (available from Hoffman-LaRoche), or Lisinopril® (available from Merck); fibroblast growth factor (FGF) antagonists, fish oil (omega 3-fatty acid), histamine antagonists, Lovastatin® (an inhibitor of HMG-COA reductase, a cholesterol-lowering drug from Merck), methotrexate, monoclonal antibodies (such as to PDGF receptors), nitroprusside, phosphodiesterase inhibitors, prostaglandin inhibitor (available from Glaxo), vascular endothelial growth factor (VEGF) or analogues thereof, various cell cycle inhibitors such as the protein product of the retinoblastoma tumor suppressor gene or analogues thereof), Seramin (a PDGF antagonist), serotonin blockers, steroids, thioprotease inhibitors, triazolopyrimidine (a PDGF antagonist), nitric oxide, alpha-interferon and genetically engineered epithelial cells.

The present invention is also directed to a method of manufacturing the medical device 10 disclosed above. More particularly, the method of the present invention first comprises providing a structure 12 adapted for the temporary or permanent introduction into a patient. The structure 12 comprises a preferably non-porous base material 14 having a surface 16 and is configured, for example, as a stent (such as a vascular stent). The structure 12 and the base material 14 have been described in detail above, and for brevity, such details will not be repeated here. Stainless steel, nitinol, tantalum, polylactic acid, polyglycolic acid and biodegradable materials are particularly preferred as the base material 14 of the structure 12.

The method of the present invention further comprises the steps of attaining a desired roughness or texture on the surface 16 of the base material 14 of the structure 12, and positing a layer 18 of a bioactive material directly upon the roughened or textured surface 16 of the base material 14. A wide range of bioactive materials useful in the layer 18 has been disclosed in detail above; again, for brevity, such detail will not be repeated. Paclitaxel, a taxane or another paclitaxel analogue, estrogen and estrogen derivatives are particularly preferred as bioactive materials in the layer 18.

The method of manufacturing a medical device 10 according to the present invention is characterized in that the resulting medical device 10 does not require or is free of any additional coating or layer atop the layer 18 of bioactive material. The method of the present invention therefore does not include any steps in which the bioactive material is covered by or contained within a time-release or containment layer. While the method of the present invention contemplates the use of a base material 14 which itself comprises a plurality of layers or constituents, such an arrangement may not be preferred in the practice of the present invention. In any event, it would be the outermost one of such plural layers or constituents which possesses the roughened or textured surface 16 on which the layer 18 of bioactive material is posited directly.

The step of directly positing the layer 18 of bioactive material on the roughened or textured surface 16 of the base material 14 can be carried out in any convenient manner. The structure 12 (or suitable portion thereof) can be dipped or soaked in an appropriate solution of the desired bioactive material, and the solvent of the solution evaporated to leave a layer 18 of the bioactive material on the roughened or textured surface 16 of the base material 14. Preferably, however, the positing step is carried out by spraying a solution of the bioactive material on the roughened or textured surface 16 of the base material 14 of the structure 12 and allowing the structure 12 to dry. While spraying may have a relatively low efficiency in transferring the bioactive material to the roughened or textured surface 16, it is adequate for the purposes of the present invention.

By way of example, paclitaxel (the particularly preferred bioactive material in the present invention) can be posited by spraying an ethanolic solution of it on the roughened or textured surface 16 of the base material 14. The solution conveniently contains about 2 to about 4 mg of paclitaxel per ml of ethanol. (The ethanol should be 100% USP grade or equivalent, not denatured alcohol or 95% ethanol.) Taking a stent of 15 mm in length and 3 mm in diameter as typical, having a textured, gross outer surface area on the order of 25 mm$^2$, spraying can be readily carried out to posit about 5 to about 500 μg, preferably 50 to 150 μg, of paclitaxel on the roughened or textured surface 16 of the base material 14. Perhaps less than about 1% of the paclitaxel is ultimately posited from solution onto the textured surface 16. The selection of suitable solvents and concentrations for other bioactive materials, or the selection of other techniques for positing other bioactive materials directly upon the roughened or textured surface 16, should be well within the skill of those in the art in view of the present disclosure. Any experimentation required should be minimal, particularly in view of the extensive testing required before devices of this type can be distributed in the U.S.

The surface 16 of the base material 14 of the structure 12 can be roughened or textured in any convenient manner, such as by etching. Preferably, however, the surface 16 is roughened or textured by abrading, for example, by abrading with an abrasive grit 24 comprising at least one of sodium bicarbonate (USP), calcium carbonate, aluminum oxide, colmanite (calcium borate), crushed glass, crushed walnut shells, or mixtures of these or other abrasive particulates. Such roughening or texturing is most easily carried out by placing the medical device 10 on a mandrel 20 in a position such that abrasive grit 24 delivered from a nozzle 22 impinges on the surface 16. The initial surface of the base material prior to roughening or texturing may be smoother than the desired surface roughness, or it may be even rougher.

The grit size and feed rate of the abrasive grit 24, the structure of the nozzle 22, the pressure at which the abrasive grit 24 is delivered from the nozzle 22, the distance of the surface 16 from the nozzle 22 and the rate of relative movement of the medical device 10 and the nozzle 22 are all factors to be considered in achieving an appropriate desired roughness or texture of the surface 16 of the base material 14 of the structure 12. By way of non-limiting example, when the base material 14 is stainless steel, the abrading step can be carried out with an abrasive grit 24 having a particle size of about 5 microns (5 μm) to about 500 microns (500 μm). More preferably, the abrading step is carried out with sodium bicarbonate (USP) having a nominal particle size of about 50 microns (50 μm), with approximately 50% greater than 40 microns (40 μm) and approximately 1% greater than 150 microns (150 μm). Such abrading is preferably carried out with the sodium bicarbonate or other abrasive grit 24 delivered at a pressure under flow of about 5 to about 200 PSI (about 34 to about 1380 KPa), most preferably about 100 PSI (about 690 KPa). Such abrading is also preferably carried out with the sodium bicarbonate or other abrasive grit 24 delivered at a grit feed rate of about 1 to about 1000 g/min, most preferably about 10 to about 15 g/min.

The carrier gas or propellant for delivery of the abrasive grit is preferably nitrogen, air or argon, and most preferably nitrogen, although other gases may be suitable as well. When the medical device 10 is configured as disclosed above, the distance from the outlet of the nozzle 22 to the center of the mandrel 20 can be about 1 to about 100 mm. A preferred nozzle 22 is the Comco Microblaster; when employed, the preferred distance from the outlet of the nozzle 22 to the center of the mandrel 20 is about 5 to about 10 mm. The Paasche LAC #3 is also useful as the nozzle 22.

To provide a uniform roughening or texturing of the surface 16 of the base material 14 of the structure 12, it is highly desirable that relative movement of the surface 16 and the nozzle 22 be provided during abrasion of the surface 16. Any pattern of motion which achieves the desired uniformity of roughness or texture may be employed. It is preferred that such motion entail both longitudinal or lengthwise movement along the structure 12 and circumferential movement or repositioning about the structure 12. Repeated longitudinal movement with repeated passes at different circumferential positions is most preferable. More particularly, abrading of the surface 16 can entail from 1 to about 50 axial passes per circumferential position, while the number of circumferential positions for such axial passes can range from about 4 to an unlimited number of circumferential positions. This last is achieved by continuous relative rotation of the surface 16 and the nozzle 22. The sweep rate of the nozzle 22 along the surface 16 can range from about 1 to about 70 mm/sec for the particular stent dimensions disclosed above.

When the base material 14 of the structure 12 is stainless steel, and the abrasive grit 24 is 50 micron sodium bicarbonate (USP), a particularly preferred combination of abrading conditions is:

Nozzle 22: Comco Microblaster
Propellant: Nitrogen gas
Pressure: 120 PSI (828 KPa) (under flow)
Spray plan: 8 equally-spaced circumferential positions
4 axial passes per circumferential position
Sweep rate: About 16 mm/sec
Grit feed rate: About 0.15 to 0.30 g/sec
Nozzle outlet to mandrel center: about 5 to 10 mm When abrading is carried out in this manner, a roughened or textured surface 16 is obtained which is thought to have a mean surface roughness (that is, a mean height of surface features) of about 10 μin. (about 250 nm) and a surface roughness range between about 1 μin. and about 100 μin. (about 25 nm and about 2.5 μm). Such a surface 16 is capable of retaining on it a highly substantial portion of bioactive material posited directly on it without requiring any additional covering or containment layer.

More particularly, the adhesion of paclitaxel to two types of stainless steel, grit abraded stents was compared to its adhesion to stents of those types whose surfaces had instead been plasma treated prior to the direct deposition of paclitaxel thereon (control stents). The coated stents of both types, that is, medical devices 10 of the present invention and control stents, were then subjected to a physical adhesion test which simulated the rate at which paclitaxel would be delivered during introduction and deployment of the stents in clinical use. The adhesion test involved passing each stent through a water-filled guiding catheter of appropriate diameter and inflating the balloon catheter to expand each stent to its intended diameter. The stents are already mounted before coating. The amount of paclitaxel remaining on each stent was then measured by spectrometry and compared to the amount of paclitaxel initially posited on each stent. Stents having surfaces 16 roughened or textured by abrasion with different abrasive grits 24 retained 84.1±10.2% of the paclitaxel originally applied, while stents having plasma treated surfaces retained only 44.3±8.7% of the paclitaxel originally applied ($p<0.0001$). This appears to demonstrate the successful retention of the layer 18 of bioactive material on the roughened or textured surface 16 of the base material 14 of the structure 12 of the medical device 10 of the present invention.

In view of the foregoing disclosure, those skilled in the art should readily be able to perform any trial-and-error testing to obtain the optimal processing conditions for any desired combination of particular base materials 14 and bioactive materials. Such testing simply requires roughening or texturing the surface 16 of a particular base material 14 in a selected manner, applying a layer 18 of a particular bioactive material to the roughened or textured surface 16 and measuring the retention of bioactive material on the roughened or textured surface 16 after clinical introduction and deployment has been mimicked.

It should be clear that the present invention provides a medical device 10 and method for manufacturing the same which is particularly advantageous over prior devices and methods for making such devices. The time and cost of manufacture of the medical device of the present invention are minimized by the absence of any steps to incorporate the bioactive material in a containment layer, or to apply a containment or time-release layer over the bioactive material. The particularly preferred use of sodium bicarbonate as the abrasive to provide roughness or texture to the surface of the base material of the structure is advantageous in the low toxicity of the sodium bicarbonate to production workers, the ease of product and waste cleanup, and the biocompatibility of any residual sodium bicarbonate. These are important advantages in their own right, but incidentally also reduce the time and cost for manufacture of the medical device 10.

The details of the construction or composition of the various elements of the medical device 10 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, most embodiments of the medical device 10 of the present invention should probably be considered to be single-use devices, rather than being reusable.

Figure 3:
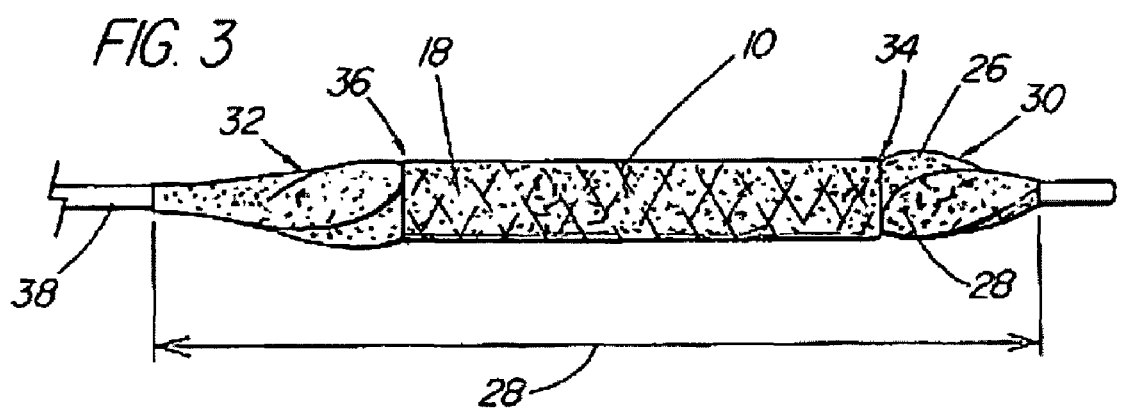
FIG. 3 depicts another preferred embodiment of the present invention in which a coated medical device such as a coated stent is mounted or positioned on another medical device such as an inflatable balloon with a bioactive material disposed on at least the outer surface of the balloon.

FIG. 3 depicts another preferred embodiment of the present invention in which a coated medical device 10 such as a coated stent is mounted or positioned on another medical device 26 such as an inflatable balloon with a bioactive material 28 disposed on the outer surface of the balloon. This bioactive material 28 is preferably a lipophilic bioactive material such as paclitaxel and other lipophilic materials such as dexamethasone and the like previously described herein. Furthermore, coated implantable medical device 10 includes a bioactive material layer posited thereon as previously described. This bioactive material layer can also be a lipophilic bioactive material such as bioactive material 28 applied to balloon medical device 26. As depicted, balloon ends 30 and 32 extend longitudinally beyond respective stent ends 34 and 36. The folded balloon ends 30 and 32 extend beyond the end of the stent ends and are coated with lipophilic bioactive material for deposition on the vessel wall extending beyond the ends of the delivered stent. The balloon 26 is preferably of a polyamide material such as nylon 12 which is available from COOK, Inc., Bloomington, Ind. The balloon 26 is attached to a catheter shaft 38, which includes a guide wire lumen as well as an inflation lumen for inflating the balloon.

Figure 4:
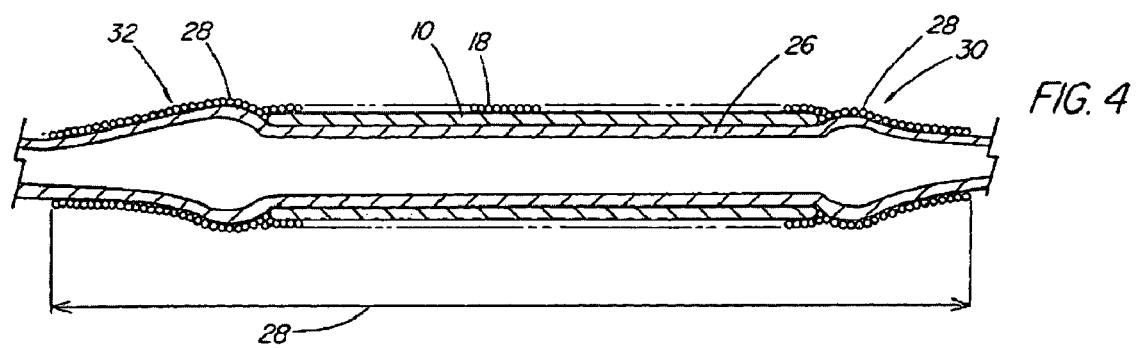
FIG. 4 depicts an enlarged and longitudinally cross-sectioned view of the medical device stent mounted on the medical device balloon of FIG. 3.

FIG. 4 depicts an enlarged and longitudinally cross-sectioned view of a medical device stent 10 mounted on medical device balloon 26 of FIG. 3. In this preferred embodiment of medical device stent 10 mounted on medical device balloon 26, the distal and proximal ends 30 and 32 of the balloon are folded and extend radially outward to the outer diameter of the compressed stent. During mounting of the stent on the balloon, the folded ends of the balloon can extend beyond the outer diameter of the stent. In this particular preferred embodiment of the present invention, the bioactive material layers 18 and 28 are of the same lipophilic bioactive material such as paclitaxel, which is applied to the stent and balloon after the stent is mounted on the balloon. Thus, the paclitaxel lipophilic bioactive material coating is applied to the outer surface of the balloon and stent. This coating process is as previously described. Thus, the paclitaxel bioactive material layer is applied to the vessel wall when the balloon and stent are expanded in the vessel at the treatment site.

Figure 5:
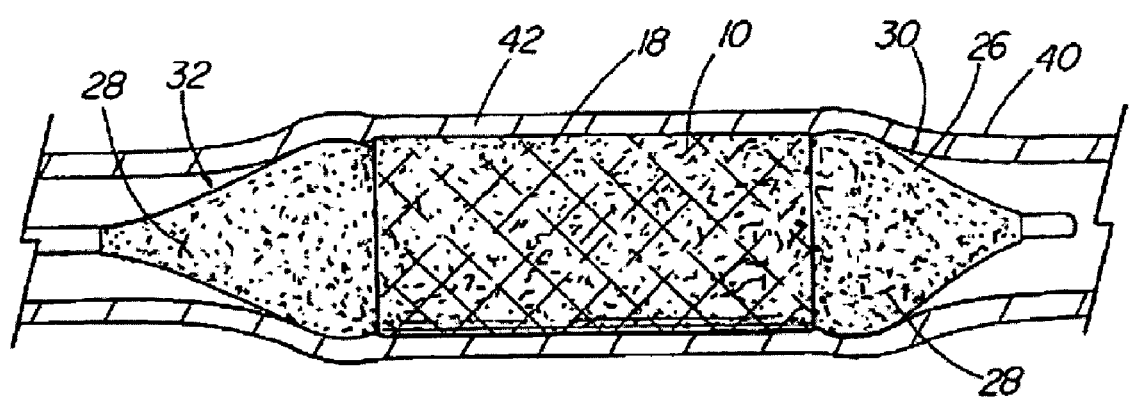
FIG. 5 depicts a coated medical device stent of the present invention mounted on medical device balloon which has been positioned in a vessel and expanded therein.

FIG. 5 depicts medical device stent 10 mounted on medical device balloon 26 which has been positioned in vessel 40 and expanded therein. As shown, that portion of vessel 42 is expanded radially outward due to the expansion of the stent and balloon to alleviate a stenotic or traumatized condition of the vessel. Portions of proximal and distal balloon ends 30 and 32 come in direct or physical contact with the radially enlarged portions of vessel wall 40. Thus, the lipophilic bioactive material 28 is applied to the enlarged portions of the vessel coming in contact therewith as well as bioactive material 18 which is on the outer surface of the medical device stent 10. This advantageously not only treats the enlarged vessel wall supported by stent 10, but also the lipophilic bioactive material is applied to the vessel extending beyond the ends of the stent and thus eliminating the undesirable edge effect associated with stent implantation.

Figure 6:
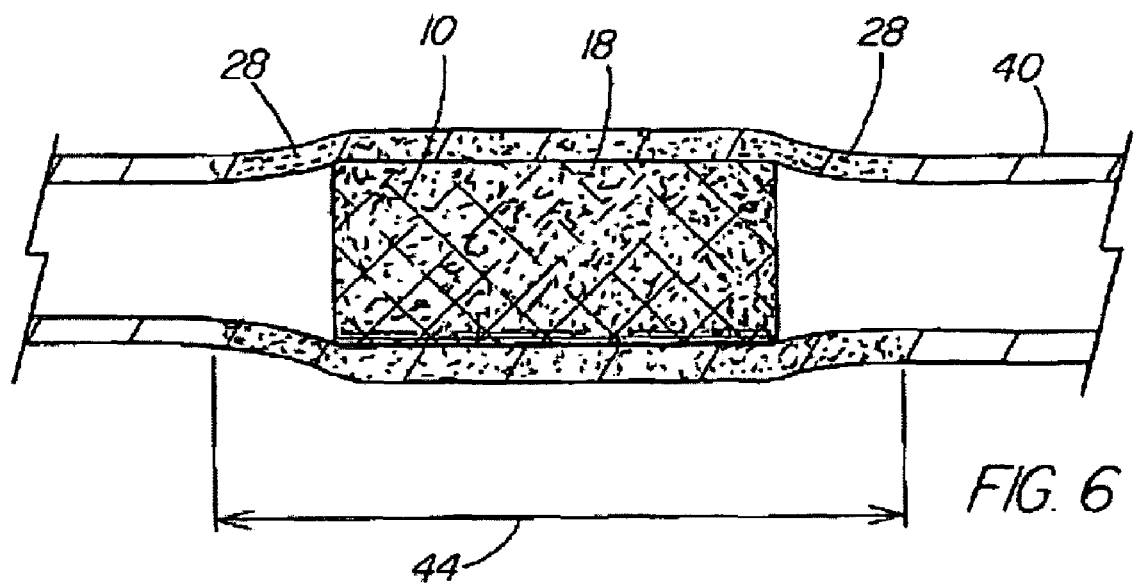
FIG. 6 depicts the coated expanded medical device stent implanted in the vessel of FIG. 5 with the medical device balloon having been deflated and removed from the treatment site.

FIG. 6 depicts expanded medical device stent 10 implanted in vessel 40 of FIG. 5 with medical device balloon 26 having been deflated and removed from the treatment site. As such, lipophilic bioactive material 18 has been applied to the vessel wall along the length of the stent, and bioactive material 28 is likewise applied to the vessel wall extending beyond the ends of the stent where the previously inflated balloon ends came in contact with the vessel wall. This drug-delivered zone 44 extending along the length of the vessel in which the balloon and stent have come in contact with the wall and to which the lipophilic bioactive material has been advantageously applied thereto for treating the traumatized or stenosed vessel and minimizing, if not eliminating, any adverse reaction due to the implantation of the stent and delivery balloon.

Figure 7:
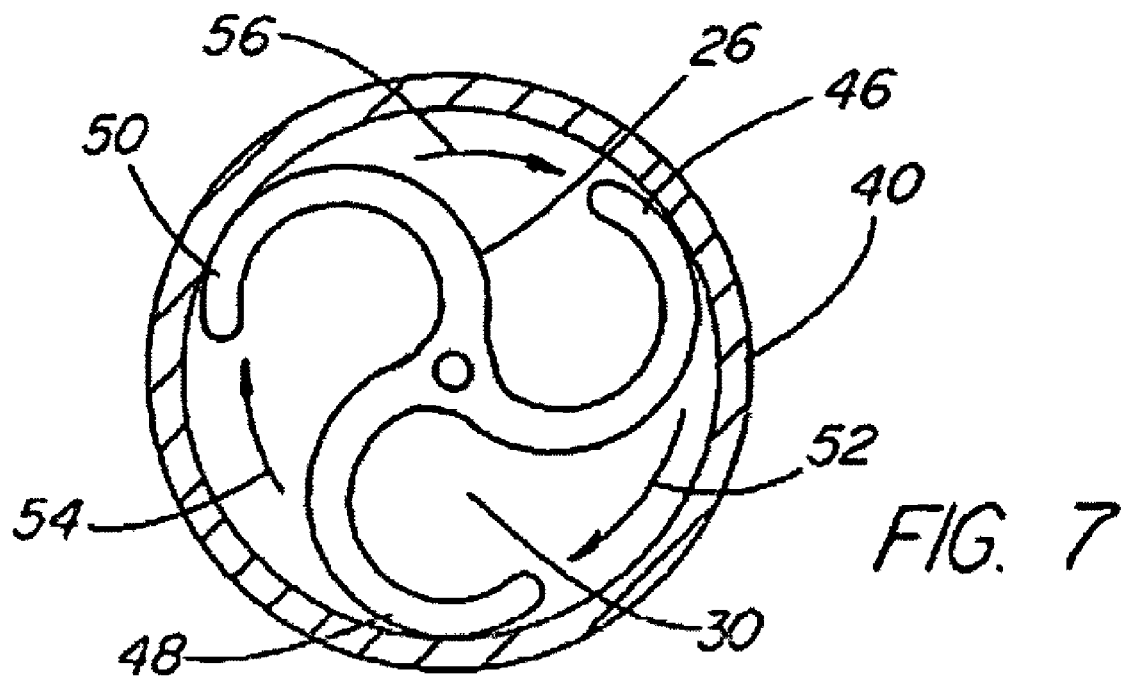
FIG. 7 depicts an enlarged cross-section end view of the balloon of FIG. in which the folds of the balloon unfurl during expansion and make contact with the inner surface of a vessel.

FIG. 7 depicts an enlarged cross-section end view of balloon 26 of FIG. 5 in which folds 46, 48 and 50 unfold or unfurl during expansion and making contact with the inner surface of vessel 40. As the balloon expands during inflation, folds 46, 48 and 50 unfurl, rotate and come in a wiping contact with the inner surface of vessel 40 in a rotational movement indicated by arrows 52, 54 and 56. The lipophilic bioactive material disposed on the surface thereof comes in contact with the inner surface of the vessel wall and is posited on the vessel surface and attached thereto with the lipophilic attraction of the cells. This rotational or wiping action further ensures a complete circumferential coating of the inner vessel surface.

Figure 8:
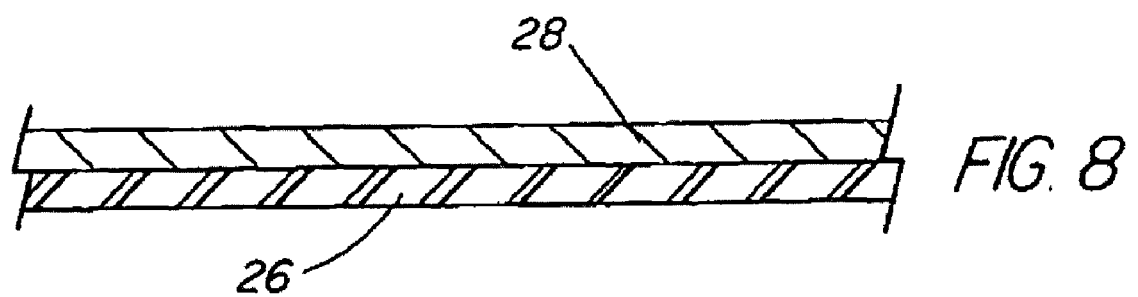
FIGS. 8-11 depict various embodiments of the bioactive material layers of the present invention posited on the base material of a medical device stent and a medical device balloon.
Figure 9:
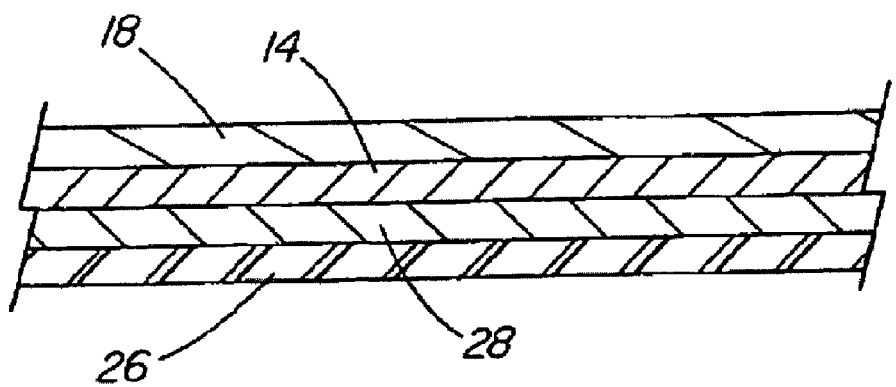
Figure 10:
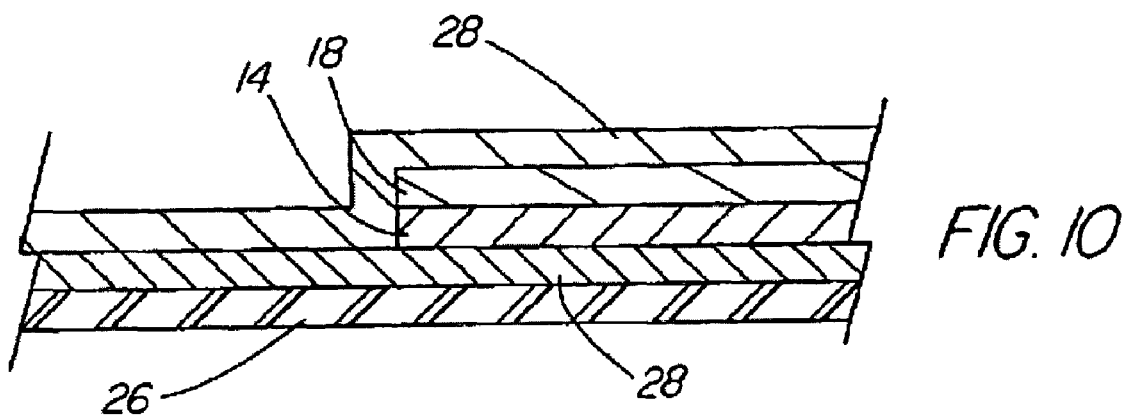
Figure 11:
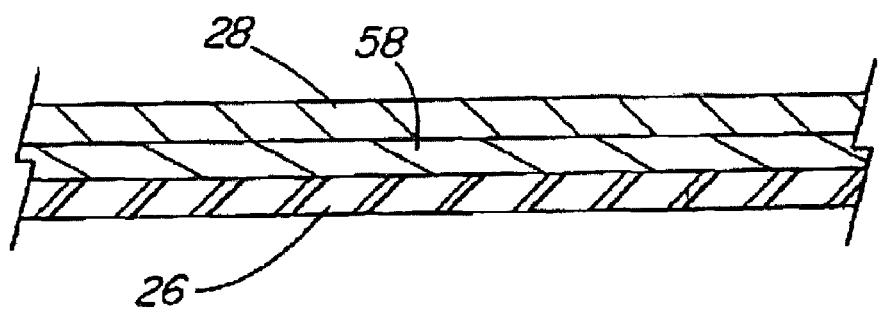

Depicted in FIGS. 8-11 are various embodiments of the bioactive material layers posited on the base material of medical device stent 10 and medical device 26. In FIG. 8, a single layer of lipophilic bioactive material 28 is posited or applied to balloon base material 26. In this embodiment, a single lipophilic coating material is applied to the surface of the balloon for a direct application to a vessel wall, for example, after the previous introduction of another stent. This balloon could be used for an angioplasty procedure without the use of a stent. FIG. 11 depicts the same balloon base material layer 26 of which a layer of hydrophilic material is posited or coated thereon. The lipophilic bioactive material layer is sprayed, posited, or disposed on the hydrophilic or slip coating layer 58. The hydrophilic layer permits easier detachment or delivery of the lipophilic layer 28 when in contact with the cells of a vessel wall.

FIG. 9 depicts another preferred embodiment of the present invention of which balloon base material 26 has lipophilic bioactive material 28 coated thereon in one operation and then medical device 10 such as a stent with base material 14 and then lipophilic bioactive material 18 is crimped or positioned around the balloon.

FIG. 10 depicts the base and lipophilic material layers of the structure of FIG. 9 with an additional layer of bioactive material 28 sprayed, posited, or disposed therein. This configuration presents an alternative embodiment for delivering greater doses of the lipophilic bioactive material to the cells located on the surface of a vessel wall.

INDUSTRIAL APPLICABILITY

The present invention is useful in the performance of various surgical procedures and in the manufacture of devices for the performance of various surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts. In particular, it is contemplated that only part of a medical device 10 according to the present invention need be coated with bioactive material. It is further contemplated that different parts of a medical device 10 could be coated with different bioactive materials.

It is also to be understood that various parts, recesses, portions, sides, segments, channels, and the like of the device can be posited with the bioactive material either singly or in combination with other bioactive, coating, or layering materials. This can be done to further control the release of the bioactive material to the delivery site. Such configurations are contemplated and disclosed in U.S. Pat. Nos. 5,380,299; 5,609,629; 5,824,049; 5,873,904; 6,096,070; 6,299,604 and are incorporated by reference herein. Likewise, presently pending patent applications claiming priority to these patents such as Ser. Nos. 08/956,715; 09/027,054; and 09/850,691 are also contemplated and incorporated by reference herein.

As previously suggested, the medical device of the present invention can also include channels, grooves, recesses, indentations, projections, buildups, and the like to increase the surface area of the device to which the bioactive material can be posited therein.

It is to be understood that paclitaxel is a lipophilic material and is rapidly taken up by cells, particularly containing lipids. Once in the cells, it binds to proteins, which helps keep the paclitaxel for subsequent use. If paclitaxel is kept around for short times, for example, 20 minutes, it can still have prolonged effects for up to, for example, 14 days. The discussion of paclitaxel can be found in various articles such as Paclitaxel Inhibits Arterial Smooth Muscle Cell Proliferation and Migration in Vitro and in Vivo Using Local Drug Delivery, Circulation, Vol. 96, No.2, Jul. 15, 1997, pp.636. Another article entitled Drug Therapy, New England Journal of Medicine, Apr. 13, 1995, pp. 1004.

What is claimed is:

1. An implantable medical device for delivering a bioactive material to a vessel wall of a patient comprising:
    a balloon catheter having an expandable balloon attached to a catheter shaft, the balloon having an expandable outer surface formed from a base material;
    a hydrophilic layer including a hydrophilic material posited on the outer surface; and
    a bioactive layer including a total of about 5 micrograms to about 500 micrograms of a lipophilic bioactive material disposed on the hydrophilic layer over the outer surface and about 0.2 micrograms to about 20 micrograms of the lipophilic bioactive material per square mm of the expanded outer surface of the balloon; the expandable balloon being free of any additional coating or layer atop the bioactive layer and
    the hydrophilic layer being positioned between the expandable outer surface and the bioactive material, wherein the hydrophilic layer is chosen such that the adhesion of the bioactive material to the hydrophilic layer is less than the adhesion of the bioactive material to the base material and wherein the hydrophilic layer enhances delivery of the bioactive material to the vessel wall.

2. The implantable medical device of claim 1, wherein the lipophilic bioactive material is an anti-angiogenic agent.

3. A method of delivering a bioactive material to an interior wall of a body vessel, the method comprising:

a. inserting a balloon catheter having an expandable balloon attached to a catheter shaft, the balloon having an expandable outer surface formed from a base material; a hydrophilic layer including a hydrophilic material posited on the outer surface; and a bioactive layer including about 0.2 micrograms to about 20 micrograms of a bioactive material per square mm of surface area of the outer surface disposed on the hydrophilic layer over the outer surface; the expandable balloon being free of any additional coating or layer atop the bioactive layer and the hydrophilic layer being positioned between the expandable outer surface and the bioactive material, wherein the hydrophilic layer is chosen such that the adhesion of the bioactive material to the hydrophilic layer is less than the adhesion of the bioactive material to the base material and wherein the hydrophilic layer enhances delivery of the bioactive material to the vessel wall;
    b. advancing the balloon within the body vessel to a treatment site within the body vessel;
    c. inflating the balloon at the treatment site to contact the bioactive material with an inner wall of the body vessel;
    d. maintaining the bioactive material on the outer surface of the inflated balloon in contact with the inner wall of the body vessel while the balloon is inflated to transfer at least a portion of the bioactive material to the inner wall of the body vessel;
    e. deflating the balloon after contacting the bioactive material with the inner wall of the body vessel; and
    f. removing the deflated balloon from the body vessel.

4. The method of claim 3, where the bioactive material is a lipophilic bioactive material selected from the group consisting of paclitaxel and dexamethasone; the hydrophilic material being configured to lessen the adhesion of the bioactive material to the balloon surface.

5. The method of claim 1, wherein the bioactive material is selected from the group consisting of paclitaxel, paclitaxel analogs, paclitaxel derivatives and pharmaceutically acceptable salts thereof.

6. The method of claim 1, the balloon catheter further comprising a first coating layer posited on at least a portion of the expandable outer surface of the expandable balloon and a second coating layer posited on at least a portion of first coating layer, where the first coating layer comprises the hydrophilic layer and the second coating layer comprises the bioactive layer and the expandable balloon structure comprises a material selected from the group consisting of: a polyamide, polyethylene terephthalate, polyurethane, a polyester, a polyorthoester, polyanhydride, polyethylene, irradiated polyethylene and or a mixture or copolymer thereof.

7. The method of claim 1, wherein the balloon catheter comprises a biocompatible polymeric material.

8. The method of claim 1, wherein the balloon catheter comprises a material selected from the group consisting of: a polyamide, polyethylene terephthalate, polyurethane, a polyester, a polyorthoester, polyanhydride, polyether sulfone, polycarbonate, polypropylene, high molecular weight polyethylene, polytetrafluoroethylene, polylactic acid, polyglycolic acid, a polyanhydride, polycaprolactone, polyhydroxybutyrate valerate, a biodegradable polymer, a protein, an extracellular matrix component, collagen, fibrin, a biologic agent, polyethylene, irradiated polyethylene and or a mixture or copolymer thereof.

9. The method of claim 3, wherein the bioactive material is selected from the group consisting of: an immunosuppressive agent, an antimetabolite agent, an antiproliferative agent, an anti-cancer chemotherapeutic agent, an antimitotic agent, a microtubule inhibitor, a smooth muscle cell inhibitor, a collagen inhibitor, a cell cycle inhibitor, an actin inhibitor, a remodeling inhibitor, a fibroblast growth factor (FGF) antagonist, a growth hormone agonist, a thrombolytic agent, an antiplatelet agent, an antithrombogenic agent, an anticoagulant agent, a histamine antagonist, a cholesterol reducing agent, an inhibitor of HMG CoA reductase, a vasodilator, a calcium channel blocker, a nitrate, a nitric oxide promoter, a dopamine agonist, an antimicrobial agent, an antibiotic agent, an agent for molecular genetic intervention, deoxyribonucleic acid, an anti-sense nucleotide, a surface glycoprotein receptor, a peptide, a protein, an enzyme, an extracellular matrix component, a cellular component, a monoclonal antibody, a phosphodiesterase inhibitor, a steroid, a prostaglandin inhibitor, a PDGF antagonist, a serotonin blocker, a thioprotease inhibitor, an angiotensin converting enzyme (ACE) inhibitor, an anti-inflammatory agent, a tissue plasminogen activator, a free radical scavenger, an iron chelator, an antioxidant, a radio-therapeutic agent, a radiopaque agent, and a radiolabelling agent.

10. The method of claim 3, wherein the bioactive material is selected from the group consisting of: paclitaxel, rapamycin, methotrexate, cytochalasin, colchicine, cyclosporine, the protein product of the retinoblastoma tumor suppressor gene, angiopeptin, a vascular endothelial growth factor (VEGF), urokinase, streptokinase, heparin, hirudin, aspirin, ticlopidine, argatroban, D-phenylalanyl-L-poly-L-arginyl chloromethyl ketone, an omega 3-fatty acid, Lovastatin, nitric oxide, Estrogen, Dopamine, bromocriptine mesylate, pergolide mesylate, streptomycin, erythromycin, vancomycin, forskolin, vapiprost, prostaglandin, prostacyclin, Seramin, triazolopyrimidine, alpha interferon, an angiotensin converting enzyme inhibitor, dexamethasone, $^{60}$CO, $^{192}$Ir, $^{32}$p, $^{111}$In, $^{90}$Y, $^{99}$mTc, an iodine-containing radiopaque compound, barium-containing radiopaque compound, gold, tantalum, platinum, tungsten, a $^{14}$C-radiolabelling compound, a $^{3}$H-radiolabelling compound, a $^{131}$1-radiolabelling compound, a $^{32}$P-radiolabelling compound, a $^{36}$S-radiolabelling compound, ascorbic acid, alphatocopherol, superoxide dismutase, deferoxyamine, a 21-aminosteroid (lasaroid), dipyridamole, nitroprusside and analogs, derivatives and pharmaceutically acceptable salts thereof.

11. The method of claim 3, wherein the bioactive material is selected from the group consisting of rapamycin, rapamycin analogs, rapamycin derivatives and pharmaceutically acceptable salts thereof.

12. The method of claim 3, where the bioactive material is a taxane bioactive material.

13. The method of claim 3, wherein the balloon is inflated for a time of up to approximately one minute.

14. An implantable medical device for delivering a bioactive material to a vessel wall of a patient comprising:

a balloon catheter having an expandable balloon attached to a catheter shaft, the balloon having an expandable outer surface formed from a base material;

a hydrophilic layer including a hydrophilic material posited on the outer surface of the balloon; and a bioactive layer disposed on the hydrophilic layer with the expandable balloon being free of any additional coating or layer atop the bioactive layer, the bioactive layer including a lipophilic bioactive material and disposed so as to expose amounts of the lipophilic bioactive material overlying the hydrophilic layer at an outermost surface over the balloon, the bioactive layer including a total of about 5 micrograms to about 500 micrograms of a lipophilic bioactive material and providing about 0.2 micrograms to about 20 micrograms of the lipophilic bioactive material per square mm of the expanded outer surface of the balloon; and the hydrophilic layer being positioned between the expandable outer surface and the bioactive material and configured to facilitate the detachment of the overlying amounts of the lipophilic bioactive material from the balloon catheter and delivery of the bioactive material to the vessel wall as compared to a corresponding balloon catheter having the bioactive material disposed directly on the surface of the balloon, wherein the hydrophilic layer is chosen such that the adhesion of the bioactive material to the hydrophilic layer is less than the adhesion of the bioactive material to the base material and wherein the hydrophilic layer enhances delivery of the bioactive material to the vessel wall.

15. A method of delivering a lipophilic bioactive material to an interior wall of a body vessel, the method comprising:

a. inserting a balloon catheter having an expandable balloon attached to a catheter shaft, the balloon having an expandable outer surface formed from a base material; a hydrophilic layer including a hydrophilic material posited on the outer surface and between the outer surface and a bioactive layer; the bioactive layer including a lipophilic bioactive material coated so as to present amounts of the lipophilic bioactive material overlying the hydrophilic layer at an outermost surface over the balloon catheter, the bioactive layer including about 0.2 micrograms to about 20 micrograms of the lipophilic bioactive material per square mm of surface area of the outer surface; the expandable balloon being free of any additional coating or layer atop the bioactive layer and the hydrophilic layer being configured to lessen the adhesion of the overlying amounts of the bioactive material to the balloon catheter and facilitate delivery of the bioactive material to the vessel wall as compared to a corresponding balloon catheter having the bioactive material disposed directly on the surface of the balloon;

b. advancing the balloon within the body vessel to a treatment site within the body vessel;

c. inflating the balloon at the treatment site to directly contact the lipophilic bioactive material overlying the hydrophilic layer with an inner wall of the body vessel;

d. maintaining the bioactive material on the outer surface of the inflated balloon in contact with the inner wall of the body vessel while the balloon is inflated to transfer at least a portion of the bioactive material to the inner wall of the body vessel;

e. deflating the balloon after contacting the bioactive material with the inner wall of the body vessel; and f. removing the deflated balloon from the body vessel.

* * * * *

UNITED STATES PATENT AND TRADEMARK OFFICE
CERTIFICATE OF CORRECTION

| | | |
|---|---|---|
| PATENT NO. | : 7,731,685 B2 | Page 1 of 1 |
| APPLICATION NO. | : 11/234702 | |
| DATED | : June 8, 2010 | |
| INVENTOR(S) | : Anthony O. Ragheb et al. | |

It is certified that error appears in the above-identified patent and that said Letters Patent is hereby corrected as shown below:

In column 20, claim 5, line 36, replace "claim 1" with --claim 4--.

In column 20, claim 6, line 40, replace "claim 1" with --claim 4--.

In column 20, claim 7, line 51, replace "claim 1" with --claim 4--.

In column 20, claim 8, line 53, replace "claim 1" with --claim 4--.

Signed and Sealed this

Seventeenth Day of August, 2010

David J. Kappos
*Director of the United States Patent and Trademark Office*